US011690572B2

(12) United States Patent
Matsumoto et al.

(10) Patent No.: US 11,690,572 B2
(45) Date of Patent: Jul. 4, 2023

(54) FLUSH DEVICE AND IRRIGATION LINE

(71) Applicant: NIPRO Corporation, Osaka (JP)

(72) Inventors: Yasushi Matsumoto, Miyagi (JP); Kuniaki Matsumoto, Osaka (JP)

(73) Assignee: NIPRO Corporation, Osaka (JP)

( * ) Notice: Subject to any disclaimer, the term of this patent is extended or adjusted under 35 U.S.C. 154(b) by 330 days.

(21) Appl. No.: 16/762,287

(22) PCT Filed: Sep. 11, 2018

(86) PCT No.: PCT/JP2018/033625
§ 371 (c)(1),
(2) Date: May 7, 2020

(87) PCT Pub. No.: WO2019/092979
PCT Pub. Date: May 16, 2019

(65) Prior Publication Data
US 2020/0352512 A1     Nov. 12, 2020

(30) Foreign Application Priority Data
Nov. 9, 2017  (JP) .................................. 2017-216698

(51) Int. Cl.
*A61M 5/168*   (2006.01)
*A61B 5/00*    (2006.01)
(Continued)

(52) U.S. Cl.
CPC ......... *A61B 5/6852* (2013.01); *A61M 3/0279* (2013.01); *A61M 5/16804* (2013.01);
(Continued)

(58) Field of Classification Search
CPC ...... A61M 39/10; A61M 39/225; A61M 5/14; A61M 5/16804; A61M 2039/1061; A61M 2039/1077; A61M 39/284
See application file for complete search history.

(56) References Cited

U.S. PATENT DOCUMENTS

| | | |
|---|---|---|
| 4,192,303 A | 3/1980 | Young et al. |
| 4,718,634 A | 1/1988 | Bond |

(Continued)

FOREIGN PATENT DOCUMENTS

| | | |
|---|---|---|
| EP | 0 006 761 A1 | 1/1980 |
| JP | 55-500411 | 7/1980 |

(Continued)

OTHER PUBLICATIONS

International Search Report dated Oct. 16, 2018 in corresponding International Application No. PCT/JP2018/033625.
International Preliminary Report on Patentability dated May 12, 2020 in corresponding PCT Application No. PCT/JP2018/033625.
Extended European Search Report dated Jul. 9, 2021 in corresponding European Patent Application No. 18875996.3.

*Primary Examiner* — Deanna K Hall
(74) *Attorney, Agent, or Firm* — Fox Rothschild LLP

(57) ABSTRACT

A flush device including: a first housing provided with a first flow path; a second housing provided with a second flow path, the second housing being coupled to the first housing; a flow control device including a protrusion and a through hole connecting the first flow path to the second flow path in fluid communication; and an elastic member provided around the base of the flow control device to seal off a space between the first and the second flow paths. The elastic member is deformed to further connect the first and second flow paths in fluid communication. The first housing has an inner periphery provided with fitting receiving portions each being fitted to each of the fitting projections of the protrusion. According to this structure, the flush device can discharge a chemical liquid at a flow rate close to a defined amount.

8 Claims, 14 Drawing Sheets

(51) Int. Cl.
  *A61M 3/02* (2006.01)
  *A61M 39/10* (2006.01)
  *A61M 39/22* (2006.01)
  *F16L 33/03* (2006.01)
  A61B 5/0215 (2006.01)
  A61B 5/03 (2006.01)

(52) U.S. Cl.
  CPC .......... *A61M 39/10* (2013.01); *A61M 39/223* (2013.01); *F16L 33/03* (2013.01); *A61B 5/0215* (2013.01); *A61B 5/036* (2013.01); *A61M 2039/229* (2013.01); *A61M 2205/0216* (2013.01); *A61M 2230/30* (2013.01)

(56) References Cited

U.S. PATENT DOCUMENTS

| | | | |
|---|---|---|---|
| 4,934,375 A | | 6/1990 | Cole et al. |
| 5,820,565 A | * | 10/1998 | McArthur ................. F16K 7/06 251/335.1 |
| 2009/0018513 A1 | | 1/2009 | Fujii et al. |
| 2010/0007134 A1 | * | 1/2010 | Elton ................... A61M 39/22 285/31 |

FOREIGN PATENT DOCUMENTS

| | | |
|---|---|---|
| JP | 2-7936 A | 1/1990 |
| WO | 80/00123 A1 | 2/1980 |
| WO | 2007/083599 A1 | 7/2007 |

* cited by examiner

FLUSH DEVICE AND IRRIGATION LINE

TECHNICAL FIELD

The present invention relates to a flush device and an irrigation line including the flush device.

BACKGROUND

In irrigation lines (also referred to as pressure monitoring tube sets) used for invasive blood pressure measurement and cerebrospinal fluid pressure measurement during surgery, blood pressure or fluid pressure is measured by converting the blood pressure or fluid pressure transmitted through a catheter and a tube into an electrical signal using a pressure transducer.

Before the catheter is inserted into the body of a patient, the tube is filled with a physiological saline solution. If a thrombus is formed in the tube or in a portion of the catheter, the thrombus may enter the body of the patient through the catheter. Thus, the irrigation line is provided with a flush device which is configured to contiguously discharge a small amount of physiological saline solution to prevent any thrombi from being formed in the tube or the like.

Patent Document 1 discloses a flush device including a first housing provided with a first flow path located on a side of a supply source of physiological saline solution, a second housing provided with a second flow path located on a side of the body of a patient, and a flow control device provided between the first flow path and the second flow path. The flow control device is provided with an orifice with a small diameter. The physiological saline solution in trace amounts coming from the first flow path is contiguously discharged toward the second flow path through the orifice. The flow control device is fixed to the second housing by ultrasonic welding.

PRIOR ART DOCUMENT

Patent Document

[Patent Document 1] U.S. Pat. No. 5,820,565 A

SUMMARY OF THE INVENTION

Problem to be Solved by the Invention

When the flow rate of the physiological saline solution discharged from the flush device is too small, a thrombus may not be prevented from being generated. On the contrary, when the flow rate is too high, a large amount of the physiological saline solution enters the body of a patient through the catheter. This may adversely affect the body of the patient. In particular, when the surgery is performed for a long time, this problem occurs remarkably. Thus, the flush device is required to discharge a physiological saline solution at a flow rate close to a defined amount.

Here, it is known that an amount of a chemical liquid discharged from the flush device can be greatly changed depending on positioning of the flow control device. The flush device of Patent Document 1 employs a structure in which the flow control device is fixed to the second housing by ultrasonic bonding, the structure having room for improvement in terms of a mechanism for positioning the flow control device.

The present invention is made to solve the above-described problem, and an object thereof is to provide a flush device capable of discharging a chemical liquid at a flow rate close to a defined amount.

Means for Solving the Problem

The present invention is directed to a flush device including:
 a first housing provided with a first flow path having a central axis;
 a second housing provided with a second flow path extending along the central axis, the second housing being coupled to the first housing;
 a flow control device having:
  a base located between the first flow path and the second flow path,
  a protrusion having a base end on a side of the base and a leading end located inside the first flow path, the protrusion extending along a central axis from the base end toward the leading end, and
  a through hole extending along the central axis through both the base and the protrusion to connect the first flow path to the second flow path in fluid communication; and
 an elastic member provided around the base of the flow control device to seal off a space between the first flow path and the second flow path;
 wherein the elastic member is configured to be deformable to form a gap between the elastic member and an outer periphery of the base of the flow control device, thereby forming a bypass flow path for further fluid communication between the first flow path and the second flow path, and
 the protrusion of the flow control device is provided on its outer periphery with a plurality of fitting projections, and
 the first housing has an inner periphery defining the first flow path, the inner periphery being provided with a plurality of fitting receiving portions each being fitted to each of the plurality of fitting projections.

According to the present invention, the fitting projections of the flow control device are fitted to the fitting receiving portions of the first housing, so that the flow control device can be disposed with the through hole extending along the central axis of the first housing. Thus, a flush device can be realized for discharging a chemical liquid at a flow rate closer to a defined amount through the flow control device.

EMBODIMENT FOR CARRYING OUT THE INVENTION

Hereinafter, embodiments of the present invention will be specifically described with reference to the accompanying drawings.

First Embodiment (1. Irrigation Line)

Figure 1:
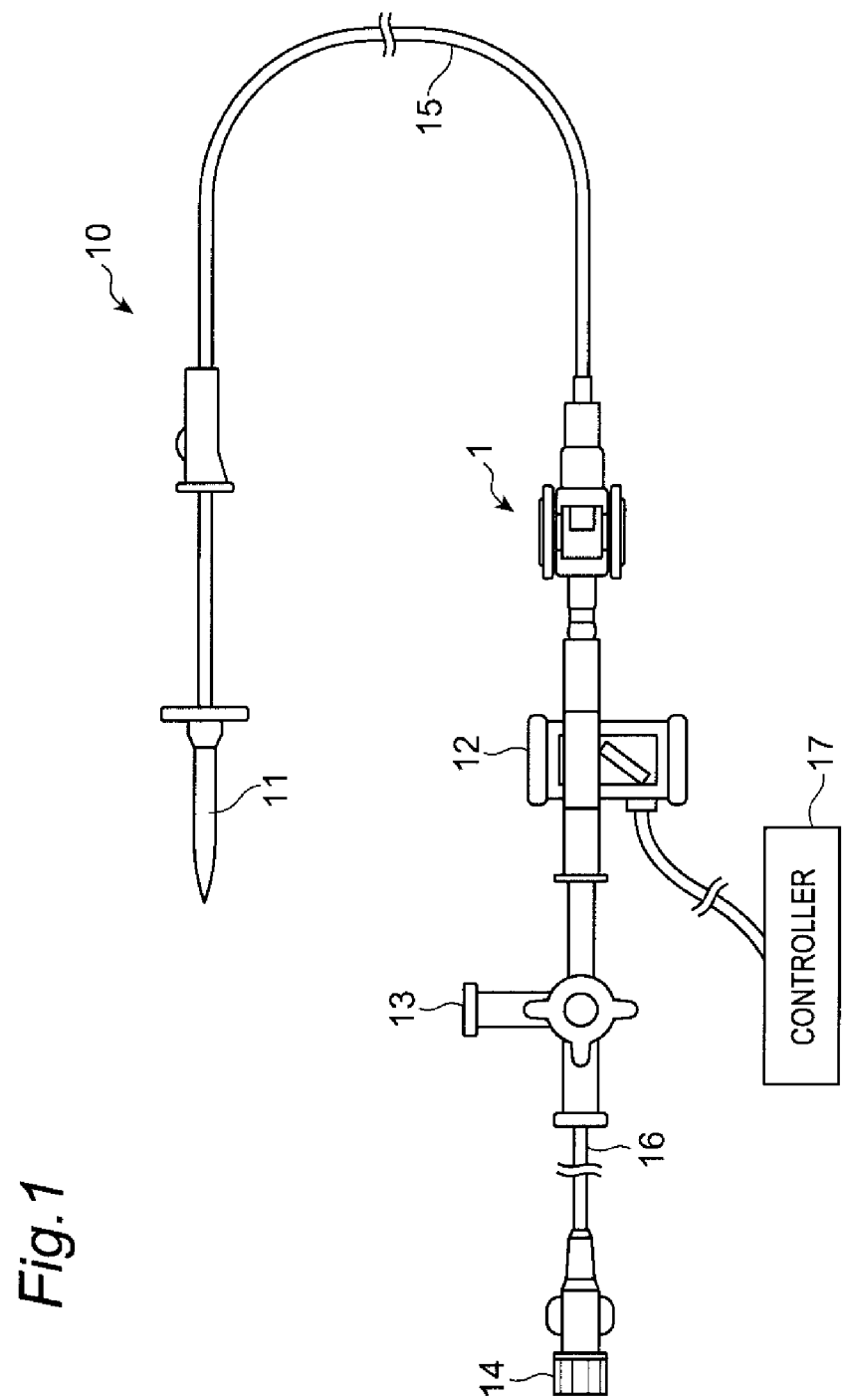
FIG. 1 is a diagram illustrating an irrigation line provided with a flush device according to a first embodiment of the present invention.

FIG. 1 illustrates an irrigation line 10 provided with a flush device 1 according to a first embodiment of the present invention. The irrigation line 10 includes a bottle needle 11, a pressure transducer 12, a three-way stopcock 13, a connector 14, and the like, along with the flush device 1. The bottle needle 11 and the flush device 1 are connected to each other with a tube 15, and the three-way stopcock 13 and the connector 14 are connected to each other with a tube 16. The flush device 1, the pressure transducer 12, and the three-way stopcock 13 may be directly connected to each other. The connector 14 is connected to a chemical liquid source (not shown).

The irrigation line 10 provided with the pressure transducer 12 may be particularly referred to as a pressure monitoring tube set. However, in the present specification, the irrigation line 10 may not include the pressure transducer 12. The irrigation line 10 may be used for invasive blood pressure measurement and cerebrospinal fluid pressure measurement during surgery.

The pressure transducer 12 is connected to a controller 17. The pressure transducer 12 converts blood pressure or fluid pressure transmitted through the bottle needle 11 and the tube 15 into an electric signal and transmits it to the controller 17. The controller 17 includes a CPU (central processing unit), a memory, a monitor, and the like, and is configured to digitally process the transmitted electric signal and display the blood pressure or the fluid pressure on the monitor. While in the present embodiment, the pressure transducer 12 is attached detachably from the irrigation line 10, it may be integrated with the irrigation line 10.

(2. Flush Device)

As illustrated in FIGS. 2 to 7, the flush device 1 includes a casing 2, a flow control device 3, an elastic member 4, and a pair of wings 5, 5. The flush device 1 is configured to contiguously discharge a small amount of chemical liquid through the flow control device 3. The flow control device 3 and the elastic member 4 are accommodated in the casing 2. The pair of wings 5, 5 is attached to the casing 2. FIGS. 2 to 7 illustrate the flush device 1 with the pair of wings 5, 5 closed.

The casing 2, the flow control device 3, and the pair of wings 5, 5 may be made of a resin material, such as ABS resin, polycarbonate resin, etc. The elastic member 4 may be made of an elastomeric material, such as silicone.

In the following description of the flush device 1, a chemical liquid source side of a position where the flush device 1 is disposed in the irrigation line 10 is referred to as an upstream side, and a bottle needle 11 side of a position where the flush device 1 is disposed in the irrigation line 10 is referred to as a downstream side. For convenience, two directions perpendicular to the direction extending from the upstream side to the downstream side (longitudinal direction) can be defined, one direction extending through the pair of wings 5, 5, being referred to as a horizontal direction, and another direction perpendicular to the longitudinal direction and the horizontal direction, being referred to as a vertical direction.

[2-1. Casing]

The casing 2 includes a first housing 6 and a second housing 7 that are coupled to each other. The first housing 6 is disposed on the upstream side, and the second housing 7 is disposed on the downstream side.

Figure 7:
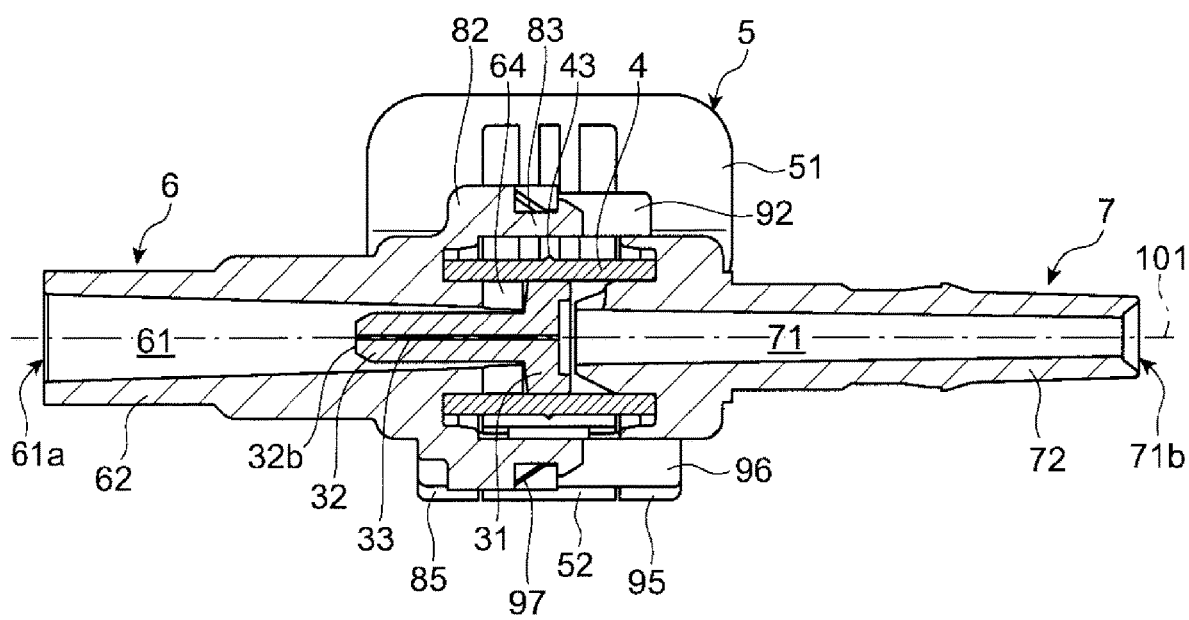
FIG. 7 is a cross-sectional view taken along line A-A and viewed in a direction of the arrow in FIG. 6.
Figure 8:
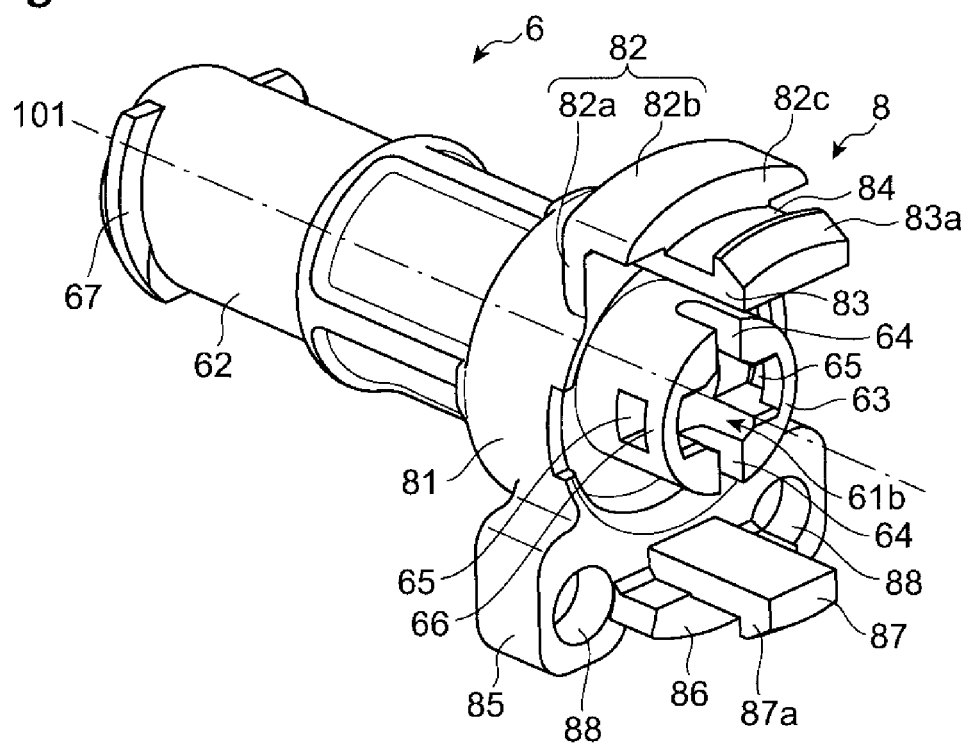
FIG. 8 is a perspective view illustrating a first housing.

As illustrated in FIGS. 7 and 8, the first housing 6 includes an elongated body 62 having a first flow path 61 inside. The first flow path 61 has a central axis 101, and the body 62 of the first housing 6 extends along the central axis 101. In the first housing 6, the direction in which the central axis 101 extends is referred to as an axial direction of the first housing 6, and any direction orthogonal to the axial direction is referred to as a radial direction of the first housing 6.

The first flow path 61 extends in a tapered shape from the upstream side to the downstream side. The first flow path 61 is provided at one end (upstream end) with an inlet 61a, and at the other end (downstream end) with an outlet 61b. The inlet 61a of the first flow path 61 serves as an inlet of the flush device 1. The inlet 61a of the first flow path 61 is circular. The outlet 61b of the first flow path 61 is formed crisscross (in a cross shape). The body 62 has a downstream end portion 63 defining the outlet 61b of the first flow path 61, to which the flow control device 3 is attached. The outlet 61b formed crisscross includes a hole extending in the vertical direction, the hole communicating with upper and lower slot grooves 64, 64 extending in the axial direction (to the upstream side) from a downstream end surface of the body 62. The slot grooves 64, 64 extend radially through a peripheral wall of the body 62.

The downstream end portion 63 of the first housing 6 includes a plurality of holes 65 provided on an inner periphery defining the first flow path 61 of the body 62. The hole 65 function as a fitting receiving portion for fitting and fixing the flow control device 3 to the first housing 6. The hole 65 have a rectangular shape when viewed laterally. The plurality of holes 65 is preferably provided at equal intervals in a circumferential direction. In the present embodiment, two holes 65 are provided on the left and right sides at 180 degree intervals. In the present embodiment, the hole 65 is a through hole passing through the peripheral wall of the body 62 in the radial direction. In another embodiment, the hole 65 may be a non-through (blind) hole that does not pass through the peripheral wall of the body 62 in the radial direction. Here, a part of the peripheral wall of the body 62, located on the downstream side of the hole 65, is referred to as a spacer receiving portion 66.

The body 62 of the first housing 6 is provided at its upstream end with a male connector 67. The male connector 67 can be attached to a female connector (not shown) provided in the pressure transducer 12 illustrated in FIG. 1.

Figure 9:
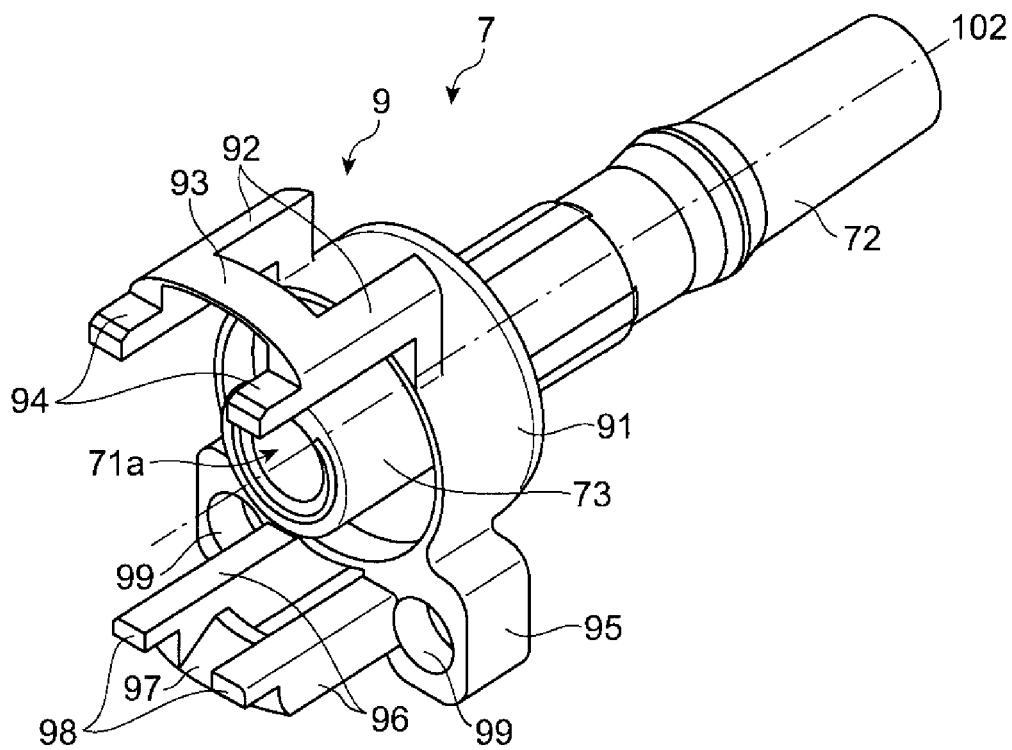
FIG. 9 is a perspective view illustrating a second housing.

As illustrated in FIGS. 7 and 9, the second housing 7 includes an elongated body 72 having a second flow path 71 inside. The second flow path 71 has a central axis 102, and the body 72 of the second housing 7 extends along the central axis 102. In the second housing 7, the direction in which the central axis 102 extends is referred to as an axial direction of the second housing 7, and any direction in a plane orthogonal to the axial direction is referred to as a radial direction of the second housing 7. The central axis 102 of the second flow path 71 extends along the central axis 101 of the first flow path 61. The central axis 102 of the second flow path 71 and the central axis 101 of the first flow path 61 may not extend completely in one straight line. Both the central axes 101, 102 may be disposed displaced (non-parallel) from each other, as long as effects of the present invention can be achieved.

The second flow path 71 extends in a tapered shape from the upstream side to the downstream side. The second flow path 71 is provided at one end (upstream end) with an inlet 71a, and at the other end (downstream end) with an outlet 71b. The inlet 71a and the outlet 71b of the second flow path 71 are circular. The outlet 71b of the second flow path 71 serves as an outlet of the flush device 1. The body 72 has an upstream end portion 73 that defines the inlet 71a of the second flow path 71 and that is located close to the flow control device 3.

Figure 2:
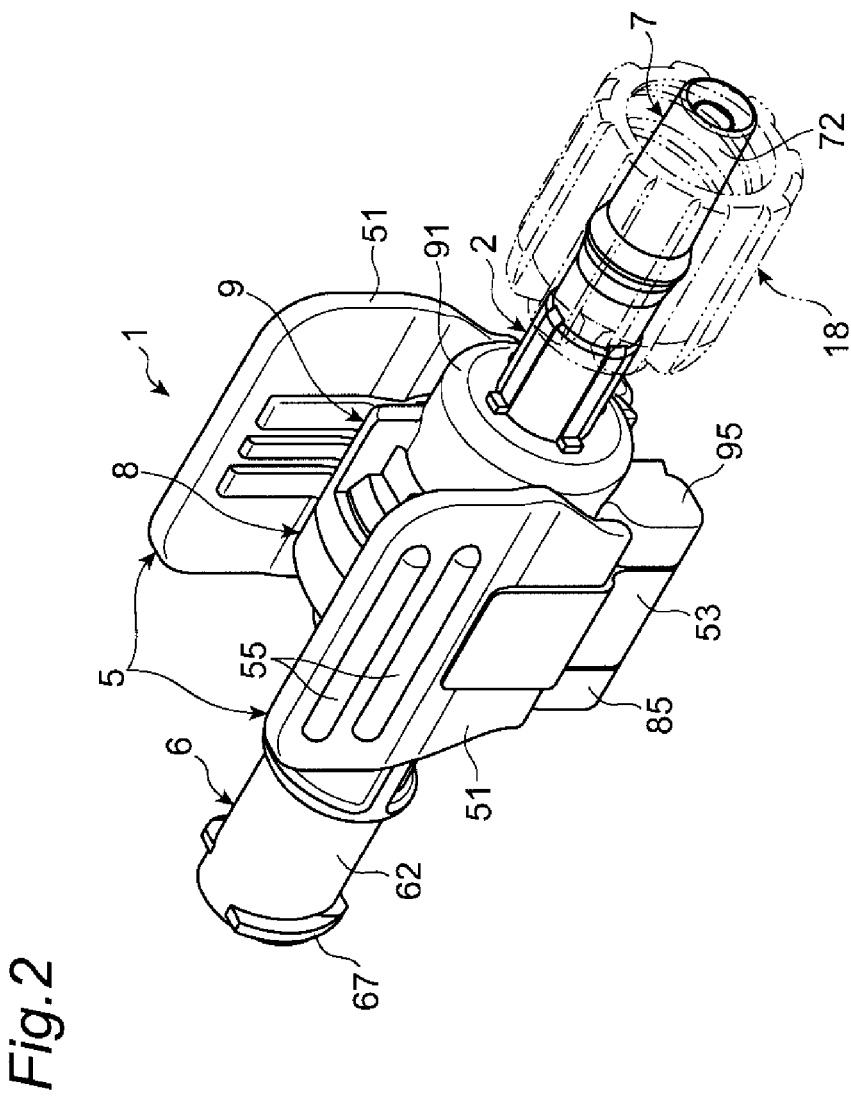
FIG. 2 is a perspective view illustrating the flush device according to the first embodiment of the present invention.

As illustrated in FIG. 2, a female connector 18 is attached to a downstream end portion of the body 72 of the second housing 7. The female connector 18 is attached to a male connector (not illustrated) provided in the tube 15 illustrated in FIG. 1.

[2-2. Coupling Mechanism]

The first housing 6 and the second housing 7 are coupled to each other by means of a coupling mechanism. In the present embodiment, the coupling mechanism includes a first coupler 8 provided at the downstream end of the first housing 6 and a second coupler 9 provided at the upstream end of the second housing 7.

As illustrated in FIG. 8, the first coupler 8 includes a cup portion 81 that opens on the downstream side in the axial direction. The cup portion 81 is provided on its downstream end with an L-shaped plate 82 as viewed from the side. The plate 82 includes a vertical plate 82a extending in the vertical direction and a horizontal plate 82b extending downstream in the axial direction. The horizontal plate 82b has a T-shaped end face 82c as viewed from the downstream side in the axial direction. The horizontal plate 82b is provided on its lower side with a tongue portion 83 extending axially downstream from the vertical plate 82a. The tongue portion 83 is provided at its downstream end with a fitting claw 83a protruding upward. The tongue portion 83 is provided in its upper surface with a recessed portion defined by the horizontal plate 82b and the fitting claw 83a. This recessed portion is referred to as a bridge receiving portion 84.

The cup portion 81 is provided in its lower downstream end with a panel 85. The panel 85 includes a horizontal plate 86 extending downstream in the axial direction. The horizontal plate 86 is provided on its upper side with a tongue portion 87 extending downstream in the axial direction from the panel 85. The tongue portion 87 is provided at its downstream end with a fitting claw 87a protruding downward. The panel 85 includes a pair of circular shaft holes 88, 88 located laterally on both side of the horizontal plate 86 and the tongue portion 87.

As illustrated in FIG. 9, the second coupler 9 includes a cup portion 91 that opens on the upstream side in the axial direction. The cup portion 91 is provided in its upper upstream end portion with a pair of beams 92, 92 laterally arranged that are fixed to the cup portion 91 and that extend upstream in the axial direction. The pair of beams 92, 92 are separated from each other by a distance equivalent to a horizontal dimension (or width) of the tongue portion 83 of the first coupler 8 in such a manner to interpose and engage with the tongue portion 83 when the first housing 6 and the second housing 7 are coupled to each other.

The second coupler 9 includes a bridge 93 connecting the beams 92, 92. When the first housing 6 is coupled to the second housing 7, the fitting claw 83a is fitted (snap-fitted) on the downstream side of the bridge 93. Then, the bridge 93 has a longitudinal dimension equivalent to a longitudinal dimension (or length) of the bridge receiving portion 84 in such a manner to fit into the bridge receiving portion 84 of the first coupler 8. As described above, the bridge 93 functions as a claw receiving portion that receives the fitting claw 83a.

On the upstream side of the bridge 93, only lower portions of the beams 92, 92 protrude upstream, constituting a pair of arms 94, 94 laterally arranged. The arms 94, 94 are fitted into respective corners of a T-shape of the horizontal plate 82b when the first housing 6 is coupled to the second housing 7. As described above, the horizontal plate 82b receives the arms 94, 94 and functions as an arm receiving portion that restricts relative rotation of the first housing 6 with respect to the second housing 7. In a preferred embodiment, the arms 94, 94 have such a longitudinal dimension as to butt a downstream surface of the vertical plate 82a of the plate 82.

The cup portion 91 is provided in its lower downstream end with a panel 95. The panel 95 includes a pair of beams 96, 96 extending upstream in the axial direction. The beams 96, 96 are separated from each other by a distance equivalent to a horizontal dimension (or width) of the tongue portion 87 of the first coupler 8 in such a manner to interpose and engage with the tongue portion 87 when the first housing 6 and the second housing 7 are coupled to each other.

The second coupler 9 includes an inclined wall 97 provided between the beams 96, 96. The inclined wall 97 extends obliquely upward with respect to the longitudinal direction as going from the upstream side toward the downstream side. When the first housing 6 is coupled to the second housing 7, the fitting claw 87a is fitted (snap-fitted) on a downstream side of the inclined wall 97. As described above, the inclined wall 97 functions as a claw receiving portion that receives the fitting claw 87a.

The beams 96, 96 have upstream ends in which only upper portions of the beams 96, 96 protrude upstream, constituting a pair of arms 98, 98 laterally arranged. The arms 98, 98 are fitted into respective corners formed by the horizontal plate 86 and the tongue portion 87 when the first housing 6 is coupled to the second housing 7. As described above, the horizontal plate 86 and the tongue portion 87 work together to receive the arms 98, 98 and function as an arm receiving portion that restricts relative rotation of the first housing 6 with respect to the second housing 7. In a preferred embodiment, the arms 98, 98 have such a longitudinal dimension as to butt a downstream surface of the panel 85. The panel 95 includes a pair of circular shaft holes 99, 99 located laterally on both side of the beams 96, 96.

[2-3. Flow Control Device]

Figure 10:
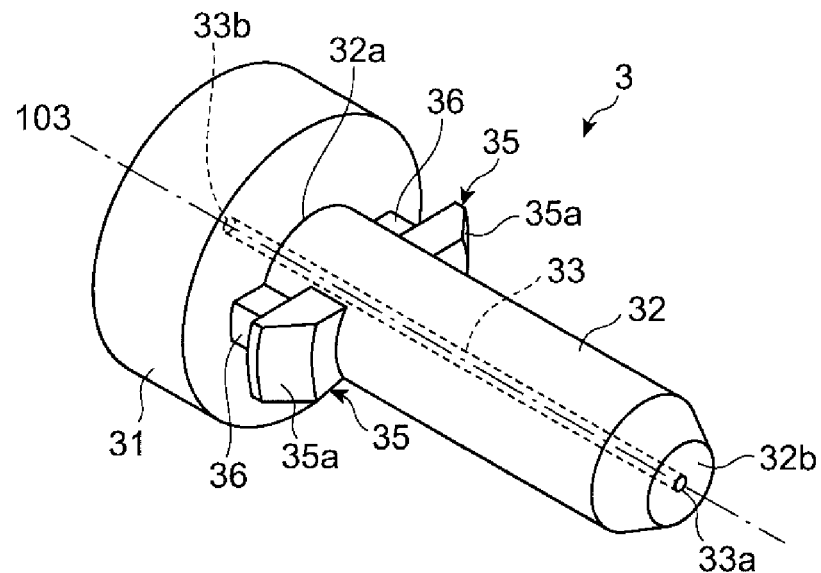
FIG. 10 is a perspective view illustrating a flow control device.
Figure 11:
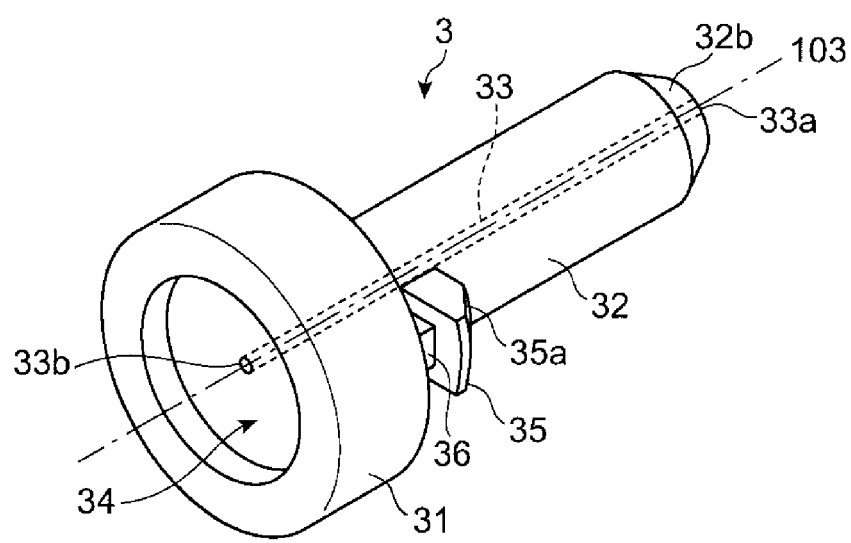
FIG. 11 is a perspective view illustrating the flow control device.
Figure 12:
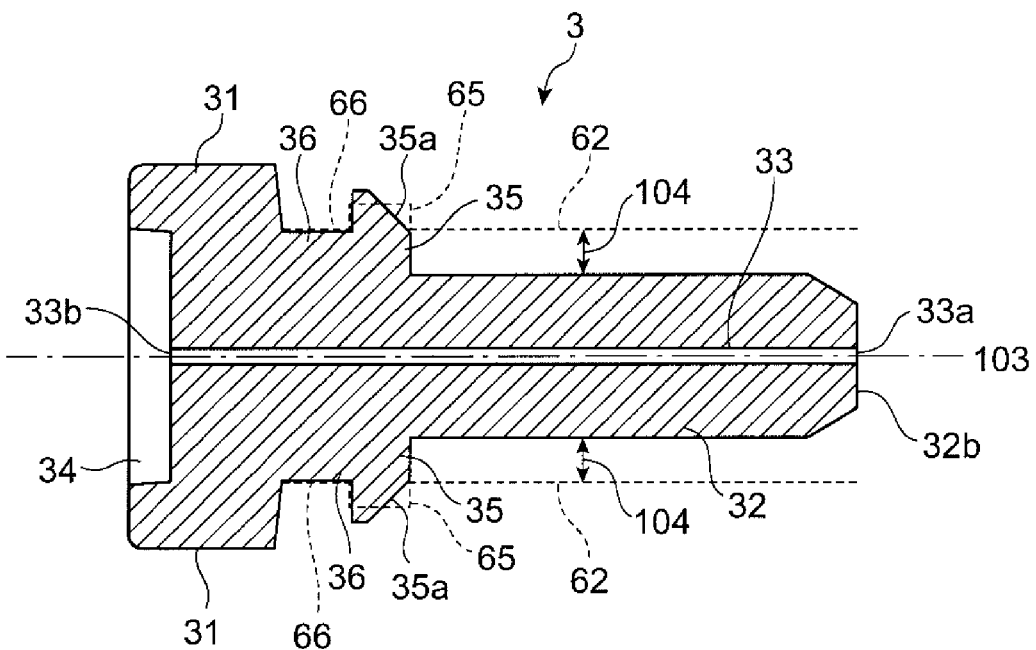
FIG. 12 is a cross-sectional view illustrating the flow control device.

The flow control device 3 includes a base 31 and a protrusion 32 extending from the base 31. The base 31 has a diameter larger than a diameter of the protrusion 32. As illustrated in FIGS. 10 and 11, in the present embodiment, the base 31 and the protrusion 32 each have a columnar shape. The base 31 is located between the first flow path 61 and the second flow path 71. The protrusion 32 has a base end 32a on a side of the base 31 and a leading end 32b on the side opposite to the base end 32a. Most of the protrusion 32 including the leading end 32b is located inside the first flow path 61. The base 31 includes a recessed portion 34. The protrusion 32 is disposed with a predetermined interval 104 away from the inner periphery of the body 62 of the first housing 6 (See FIG. 12).

The flow control device 3 is attached to the downstream end portion 63 of the first housing 6. The base 31 has a dimension (diameter) to completely cover a downstream end face of the first housing 6 as the flow control device 3 is attached to the downstream end portion 63 of the first housing 6. The base 31 preferably has a diameter substantially equivalent to a diameter of the downstream end portion 63 of the first housing 6.

The flow control device 3 is provided with a through hole 33 extending through the base 31 and the protrusion 32. The through hole 33 has such an inner diameter as to function as a capillary. The flush device 1 discharges a chemical liquid at a flow rate that decreases with decrease in diameter of the through hole 33 and with increase in length thereof. The through hole 33 has a central axis 103, and the protrusion 32 extends along the central axis 103. In the flow control device 3, a direction in which the central axis 103 extends is referred to as an axial direction of the flow control device 3, and any direction in a plane orthogonal to the axial direction is referred to as a radial direction of the flow control device 3. The central axis 103 of the through hole 33 extends along the central axis 101 of the first flow path 61 (and the central axis 102 of the second flow path 71). The central axis 103 of the through hole 33 may not extend completely in one straight line with the central axis 101 of the first flow path 61 (and the central axis 102 of the second flow path 71). The central axes 101, 102, 103 may be disposed displaced (non-parallel) from each other, as long as effects of the present invention can be achieved.

The through hole 33 connects the first flow path 61 and the second flow path 71 in fluid communication in the flush device 1. The through hole 33 has an inlet 33a and an outlet 33b. The inlet 33a communicates with the first flow path 61 provided in the first housing 6, and the outlet 33b communicates with the second flow path 71 provided in the second housing 7.

In the flow control device 3, the protrusion 32 is provided on its outer periphery with a plurality of fitting projections 35 projecting radially outward. The fitting projections 35 are fitted (snap-fitted) into the corresponding holes 65 provided in the first housing 6, so that the flow control device 3 is fixed to the first housing 6. When the plurality of holes 65 are provided at equal intervals in the circumferential direction, the plurality of fitting projections 35 are also provided at equal intervals in the circumferential direction. The number of the fitting projections 35 may be equal to that of the holes 65. The fitting projections 35 each have a shape complementary to the hole 65, and in the present embodiment, each have a shape similar to a rectangular parallelepiped. However, the fitting projections 35 are each provided with an inclined surface 35a to facilitate fitting of the fitting projections 35 into the corresponding holes 65.

In the flow control device 3, a plurality of spacers 36 are provided on the outer periphery of the protrusion 32 and on the side of the base end 32a of the plurality of fitting projections 35. The spacers 36 each have a rectangular parallelepiped shape. The spacers 36 each protrude radially outward from the outer periphery of the protrusion 32 toward the inner periphery defining the first flow path 61.

In the present embodiment, two spacers 36 are provided on the left and right sides at 180 degree intervals apart from each other, as two holes 65 are provided on the left and right sides at 180 degree intervals apart from each other. In addition, in the present embodiment, the plurality of spacers 36 each butt the inner periphery defining the first flow path 61. It is preferable that the plurality of spacers 36 each have such a dimension as to butt and bump the inner periphery. In another embodiment, a predetermined interval may exist between a radially outer end of each of the plurality of spacers 36 and the inner periphery.

[2-4. Elastic Member]

Figure 13:
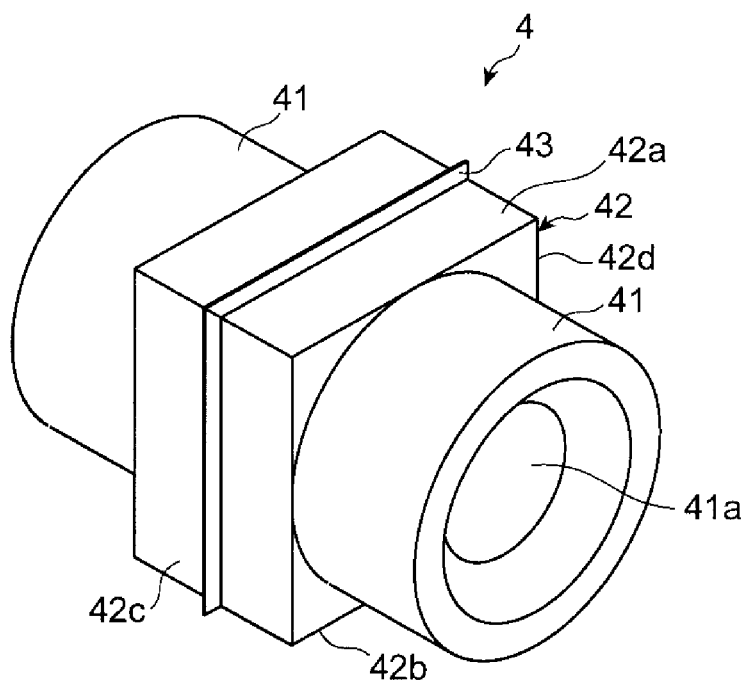
FIG. 13 is a perspective view illustrating an elastic member.
Figure 14:
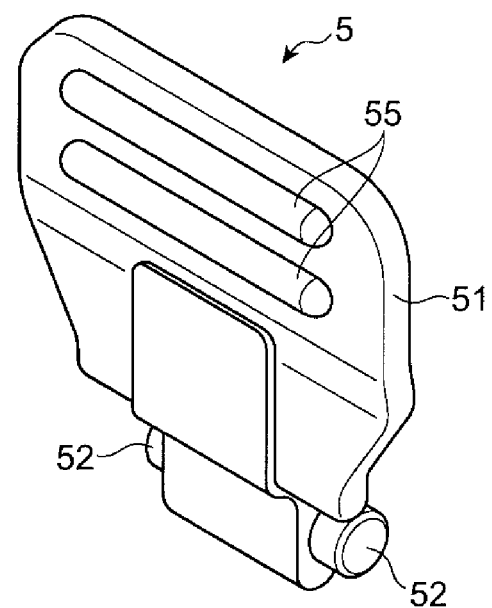
FIG. 14 is a perspective view illustrating a pair of wings.

As illustrated in FIG. 13, the elastic member 4 includes a tubular portion 41 and a block portion 42 provided around the tubular portion 41. The tubular portion 41 is provided around the base 31 of the flow control device 3. The tubular portion 41 includes a hollow portion 41a in which the base 31 and the downstream end portion 63 of the first housing 6 are biased to be accommodated. This can seal off a space between the first flow path 61 and the second flow path 71, and the first flow path 61 is connected to the second flow path 71 in fluid communication only via the through hole 33. When the base 31 and the downstream end portion 63 of the first housing 6 each have an approximately equal diameter, the elastic member 4 can suitably accommodate them. The elastic member 4 is biased to be held between the upper and lower tongue portions 83, 87 of the first coupler 8 on the upstream side, and is biased to be held between the upper and lower arms 94, 98 of the second coupler 9 on the downstream.

The block portion 42 has a square shape when viewed in the axial direction. The block portion 42 includes an upper surface 42a and a lower surface 42b that are respectively in contact with the upper and lower tongue portions 83, 87 of the first coupler 8, and side surfaces 42c, 42d orthogonal to the upper surface 42a and the lower surface 42b. The block portion 42 is provided at its axially central portion with a bump 43 throughout the circumference thereof. The bump 43 is provided integrally with the block portion 42. When the casing 2 is made of a transparent or translucent material, the bump 43 is viewed from the outside to function as a positioning marker for checking whether the elastic member 4 is disposed at a correct position. The side surfaces 42c, 42d of the block portion 42 are partially exposed to the pair of wings 5, 5 without being covered with the casing 2.

The elastic member 4 is configured to be deformed when receiving a force from the pair of wings 5, 5 to form a gap between the elastic member 4 and the outer periphery of the base 31 of the flow control device 3. This can create a bypass flow path 105 (See FIG. 17) for further fluid connection between the first flow path 61 and the second flow path 71.

[2-5. Pair of Wings]

Figure 15:
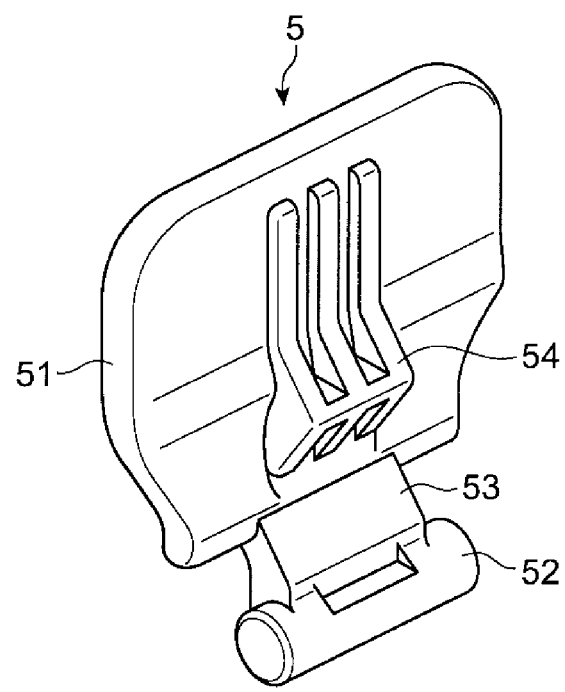
FIG. 15 is a perspective view illustrating the pair of wings.
Figure 16:
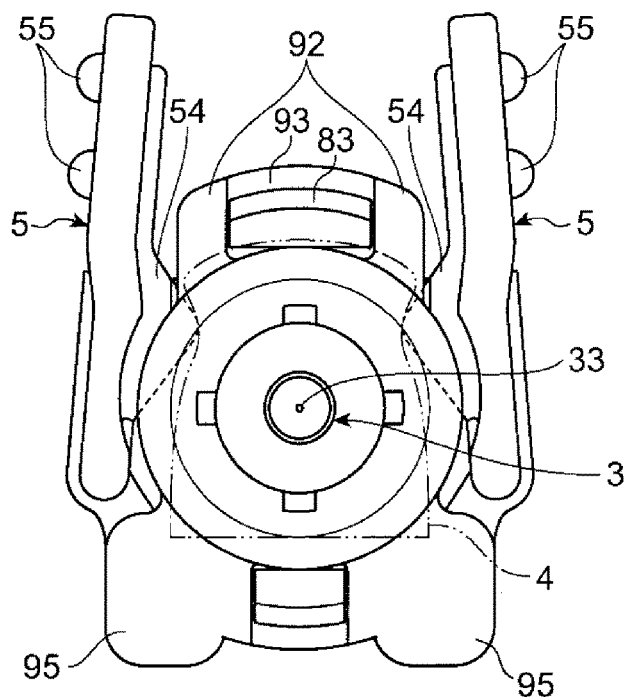
FIG. 16 is a view corresponding to FIG. 6, illustrating a state in which a pair of wings is displaced.

The pair of right and left wings 5, 5 is a member for pressing and deforming the elastic member 4. The wings 5, 5 have a shape allowing a user to pinch it with the balls of fingers, for example. As best illustrated in FIGS. 15 and 16, each of the wings 5, 5 includes a plate-shaped body 51, a cylindrical shaft portion 52 that is provided at the bottom of the body 51 and that extends parallel to the central axis 101, and a connecting portion 53 for connecting the body 51 and the shaft portion 52. The connecting portion 53 extends obliquely with respect to the body 51 when viewed in the axial direction.

The shaft portion 52 is inserted into the shaft hole 89 of the first coupler 8 and the shaft hole 99 of the second coupler 9. The shaft portion 52 has a diameter slightly smaller than a diameter of each of the shaft holes 89 and 99. The shaft portion 52 and the shaft hole 89 form a hinge mechanism. In this way the pair of wings 5, 5 can be supported by the first housing 6 and the second housing 7 so as to rotate around each shaft portion 52. In another embodiment, a hinge mechanism may be formed by providing a protrusion on each of the first coupler 8 and the second coupler 9 and fitting the protrusion to a recessed portion each provided on the shaft members.

The body 51 is provided on its inner surface with a pressing portion 54. The pressing portion 54 is a protrusion that can press each of the side surfaces 42c, 42d of the block portion 42 of the elastic member 4 when the pair of wings 5, 5 is rotated inward around the shaft portions 52, 52 toward the elastic member 4. In the present embodiment, the pressing portion 54 presses an upper portion of each of the side surfaces 42c and 42d of the block portion 42. The body 51 is provided on its outer surface with a knob 55 that is a protrusion extending along the axial direction, thereby allowing a user to easily operate the pair of wings 5, 5.

Figure 17:
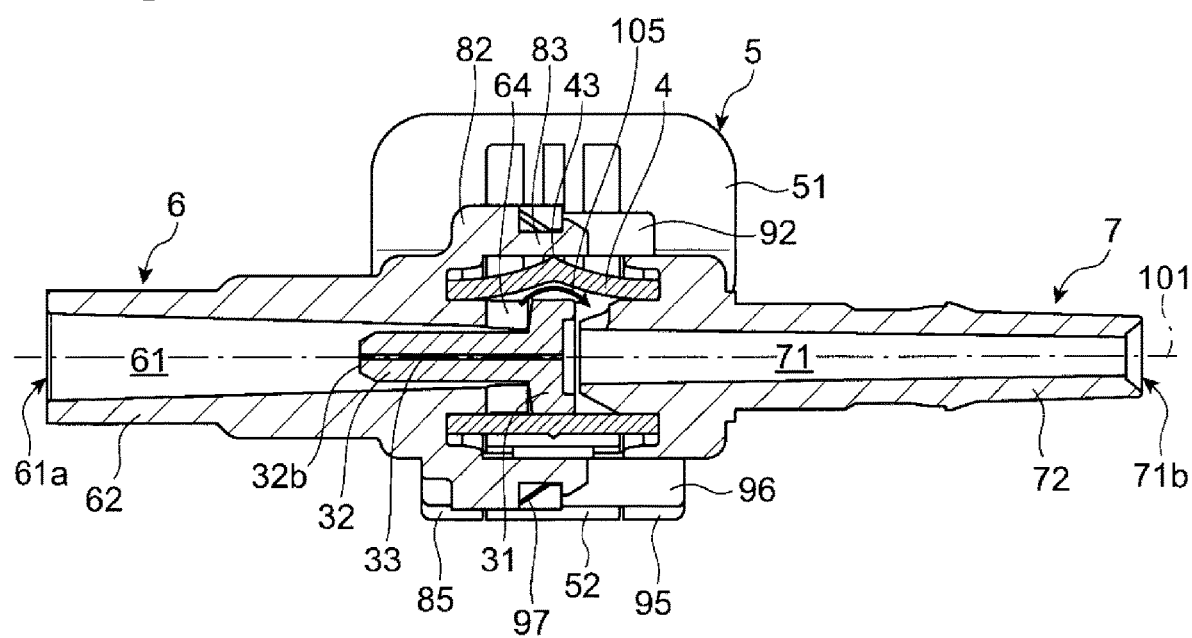
FIG. 17 is a view corresponding to FIG. 7, illustrating a state in which a pair of wings is displaced.

As illustrated in FIGS. 16 and 17, when the user pinches and rotates the pair of wings 5, 5 inward toward the elastic member 4, upper portions of the side surfaces 42c, 42d of the elastic member 4 are pressed. Then, the upper surface 42a of the elastic member 4 is deformed so as to form an upwardly convex curved surface. This can form a bypass flow path 105 for a chemical liquid, connected from the first flow path 61 to the second flow path 71 through the upper slot groove 64, and a larger amount of chemical liquid can pass through the bypass flow path 105. In this way the flush device 1 can discharge and quickly flush more chemical liquid.

[2-6. Assembly of Flush Device]

Figure 3:
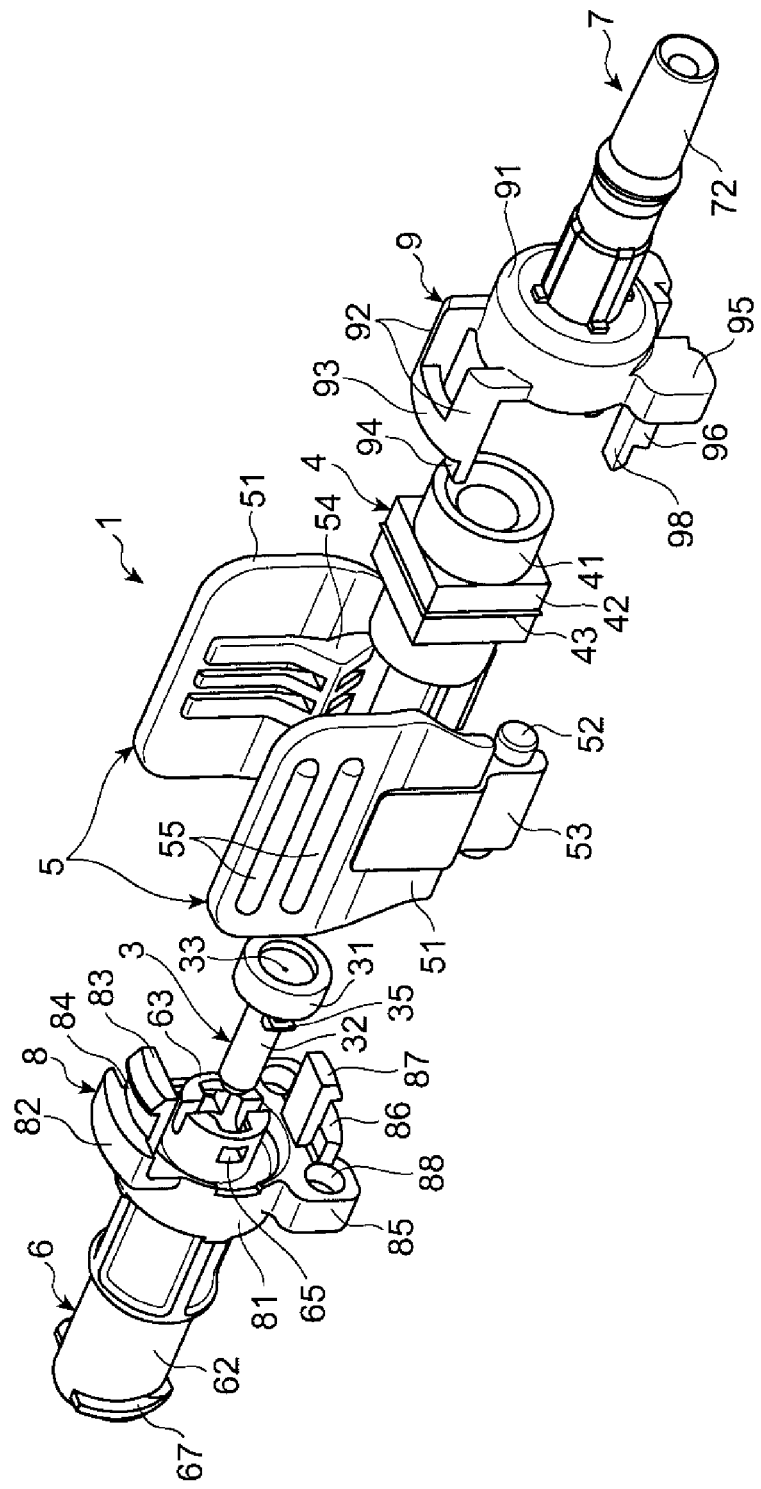
FIG. 3 is an assembly view illustrating the flush device according to the first embodiment of the present invention.
Figure 4:
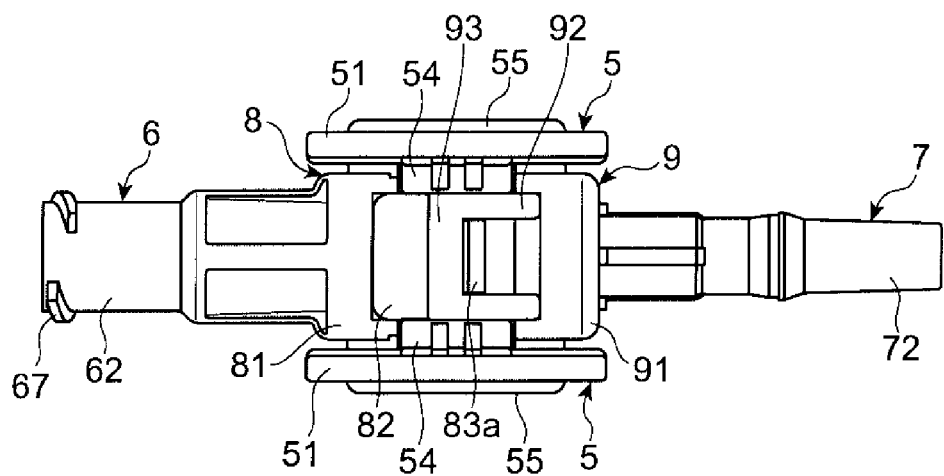
FIG. 4 is a plan view illustrating the flush device according to the first embodiment of the present invention.
Figure 5:
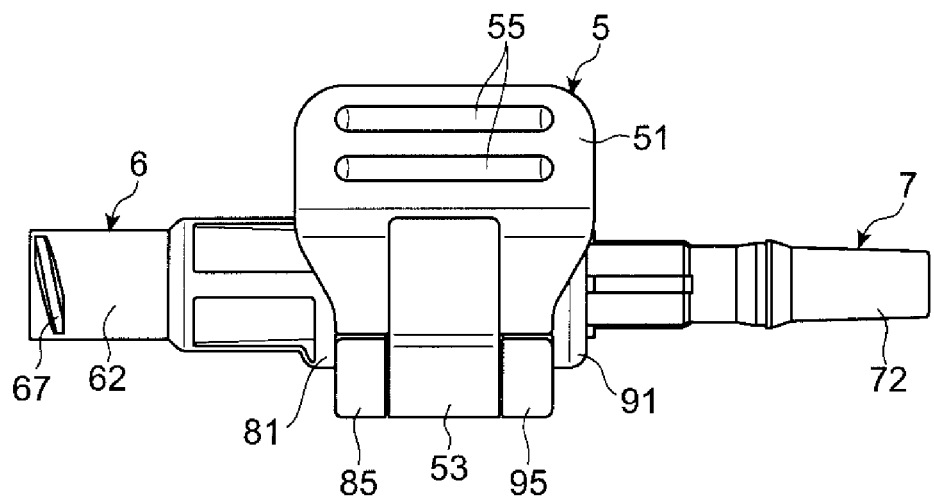
FIG. 5 is a side view illustrating the flush device according to the first embodiment of the present invention.
Figure 6:
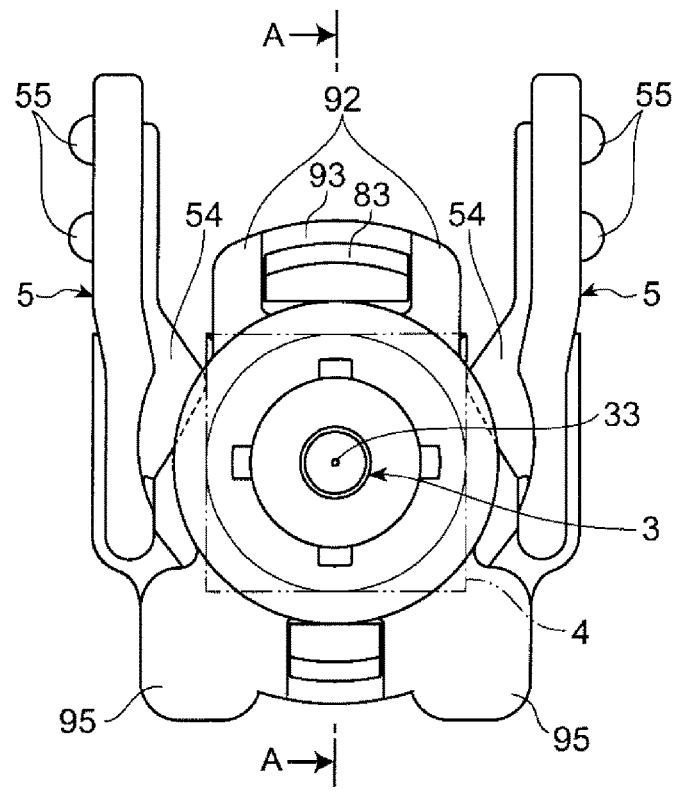
FIG. 6 is a front view illustrating the flush device according to the first embodiment of the present invention.

With reference to FIG. 3, a method for assembling the flush device 1 will be described. First, the fitting projection 35 of the flow control device 3 is fitted (snap-fitted) into the hole 65 of the first housing 6, so that the flow control device 3 is fixed to the first housing 6. This allows the flow control device 3 to be positioned in the radial direction and the axial direction, thereby the central axis 103 of the through hole 33 of the flow control device 3 extending along the central axis 101 of the first flow path 61. In the present embodiment, when the fitting projection 35 is fitted into the hole 65, the plurality of spacers 36 each butt the inner periphery defining the first flow path 61. This allows the flow control device 3 to be more reliably fixed to the first housing 6, so that the flow control device 3 is positioned with higher accuracy in the radial direction and the axial direction. When the flow control device 3 is fixed to the first housing 6, the outlet 61b of the first flow path 61 is covered with the base 31 of the flow control device 3.

Next, the base 31 of the flow control device 3 and the downstream end portion 63 of the first housing 6 are inserted into the hollow portion 41a of the tubular portion 41 of the elastic member 4. The elastic member 4 is held between the upper and lower tongue portions 83, 87 of the first coupler 8 on the upstream side, and is held between the upper and lower arms 94, 98 of the second coupler 9 on the downstream side. This allows the flow control device 3 to be more reliably fixed to the first housing 6, so that the flow control device 3 is positioned with higher accuracy in the radial direction and the axial direction. At this time, it is checked that the elastic member 4 is disposed at a correct position (in the present embodiment, the position of the base 31 of the flow control device 3) by observing the position of the bump 43 provided on the block portion 42 of the elastic member 4 from the outside.

Next, the first housing 6 is coupled to the second housing 7. Specifically, the fitting claws 83a are fitted to the downstream side of the bridge 93 (snap fitted) while the shaft portions 52, 52 are inserted into the corresponding shaft holes 88, 88 of the panel 85 and the corresponding shaft holes 99, 99 of the panel 95, and thus the bridge receiving portion 84 of the first coupler 8 is fitted to the bridge 93 of the second coupler 9. In this manner, the first housing 6 is coupled to the second housing 7, and the second housing 7 is positioned with respect to the first housing 6 in the radial direction and the axial direction, thereby the central axis 102 of the second flow path 71 extending along the central axis 101 of the first flow path 61.

When the first housing 6 is coupled to the second housing 7, the upper beams 92, 92 of the second coupler 9 interpose and engage with the upper tongue portion 83 of the first coupler 8, and the lower beams 96, 96 of the second coupler 9 interpose and engage with the lower tongue portion 87 of the first coupler 8. This allows the second housing 7 to be further positioned in the radial direction with respect to the first housing 6.

When the first housing 6 is coupled to the second housing 7, the arms 94, 94 of the second coupler 9 are further fitted into the respective corners of the T-shape of the horizontal plate 82b of the first coupler 8, and the lower arms 98, 98 of the second coupler 9 are fitted into the respective corners formed by the horizontal plate 86 and the tongue portion 87 of the first coupler 8. Accordingly, even when a force bending or twisting the casing 2 is applied, relative rotation of the first housing 6 with respect to the second housing 7 is restricted by the horizontal plate 82b on the upper side and the horizontal plate 86 and the tongue portion 87 on the lower side, and thus the second housing 7 is hardly displaced with respect to the first housing 6.

In a preferred embodiment, when the first housing 6 is coupled to the second housing 7, the arms 94, 94 of the second coupler 9 butt the downstream surface of the vertical plate 82a of the plate 82, and the lower arms 98, 98 of the second coupler 9 butt the downstream surface of the panel 85. This allows the second housing 7 to be further positioned in the axial direction with respect to the first housing 6.

Here, when the central axis 103 of the through hole 33 of the flow control device 3 extends more linearly with both the central axis 101 of the first flow path 61 of the first housing 6 and the central axis 102 of the second flow path 71 of the second housing 7, a flow rate of the chemical liquid discharged from the flow control device 3 can be made closer to a defined amount.

In the flush device 1 according to the above-described embodiment, the flow control device 3 can be positioned so that the central axis 103 of the flow control device 3 extends along the central axis 101 of the first flow path 61. In addition, the second housing 7 can be positioned with respect to the first housing 6 so that the central axis 102 of the second flow path 71 extends along the central axis 101 of the first flow path 61. In this manner, the flush device 1 capable of discharging the chemical liquid at a flow rate close to the defined amount can be realized.

In the flush device 1 according to the above-described embodiment, the flow control device 3 is fixed to the first housing 6 only by means of a mechanical joint (coupling mechanism) without forming a joint by adhesion or welding. The same applies to fixing of the second housing 7 to the first housing 6. In this manner, in the above-described embodiment, the flush device 1 can be more easily assembled. However, in another embodiment, a joint formed by adhesion or welding may be provided in addition to these mechanical joints.

Second Embodiment

Figure 18:
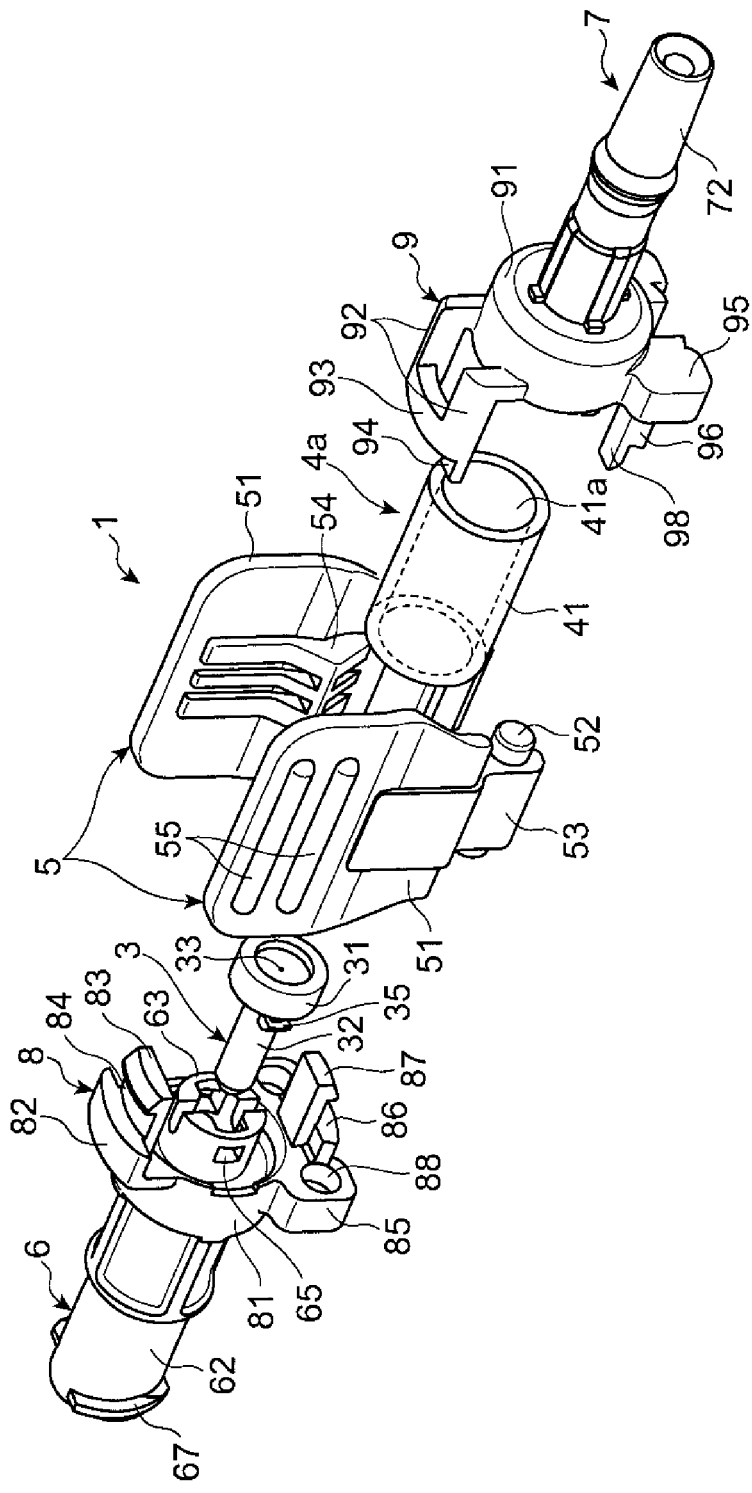
FIG. 18 is a diagram illustrating an irrigation line provided with a flush device according to a second embodiment of the present invention.
Figure 19:
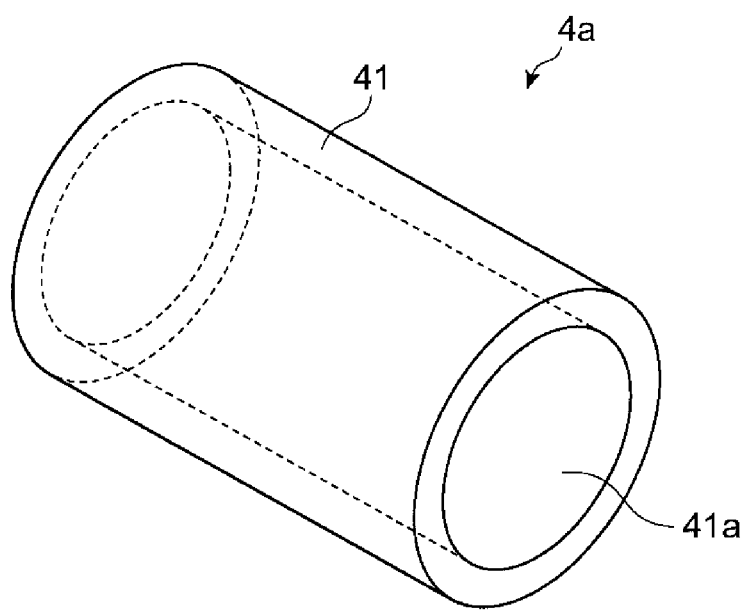
FIG. 19 is a perspective view illustrating another example of the elastic member.

FIG. 18 is a diagram illustrating an irrigation line provided with a flush device according to a second embodiment of the present invention. FIG. 19 is a perspective view illustrating another example of the elastic member. The flush device according to the second embodiment employs an elastic member 4a having a cylindrical shape instead of the elastic member 4 including the block portion 42. Other configurations are the same as those of the flush device according to the first embodiment, and thus duplicated description will be eliminated.

Figure 20:
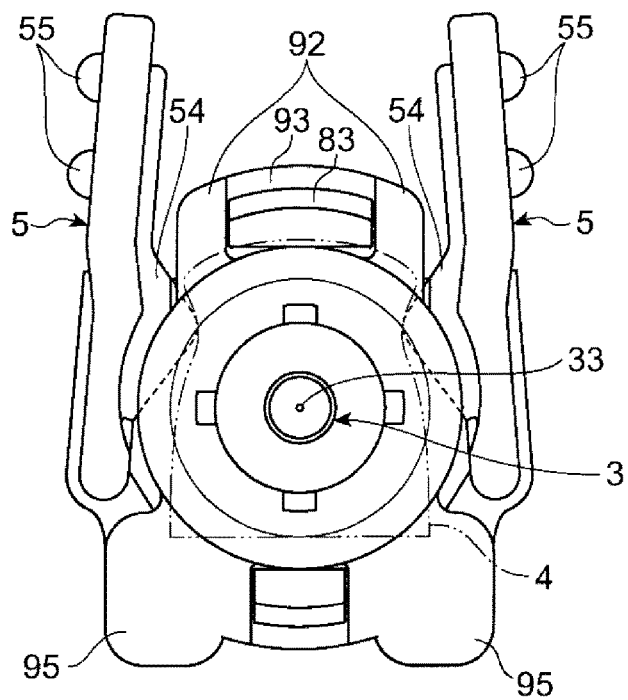
FIG. 20 is a front view illustrating the flush device according to the second embodiment of the present invention.
Figure 21:
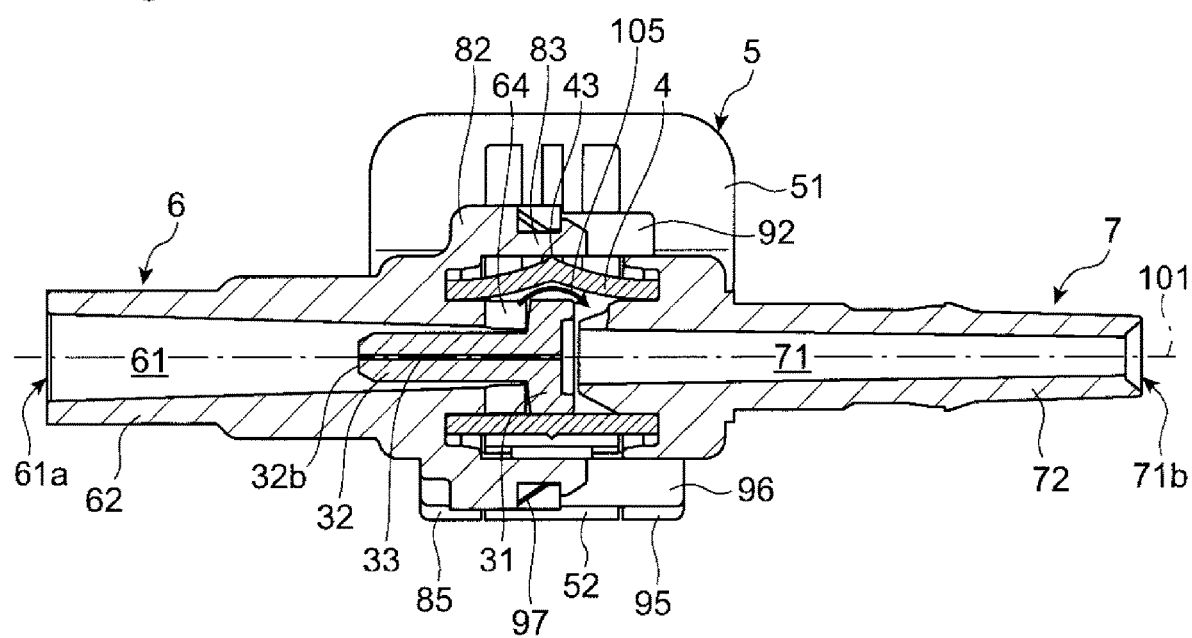
FIG. 21 is a cross-sectional view taken along line A-A and viewed in a direction of the arrow in FIG. 20.

As illustrated in FIG. 19, the elastic member 4a includes a tubular portion 41 provided with a hollow portion 41a, and is made of, for example, an elastomeric material such as silicone. As illustrated in FIGS. 20 and 21, the elastic member 4a is provided around the base 31 of the flow control device 3, and the base 31 and the downstream end portion 63 of the first housing 6 are biased to be accommodated in the hollow portion 41a. This can seal off a space between the first flow path 61 and the second flow path 71, and the first flow path 61 is connected to the second flow path 71 in fluid communication only via the through hole 33. When the base 31 has a diameter approximately equal to a diameter of the downstream end portion 63 of the first housing 6, the elastic member 4a can appropriately accommodate them.

Figure 22:
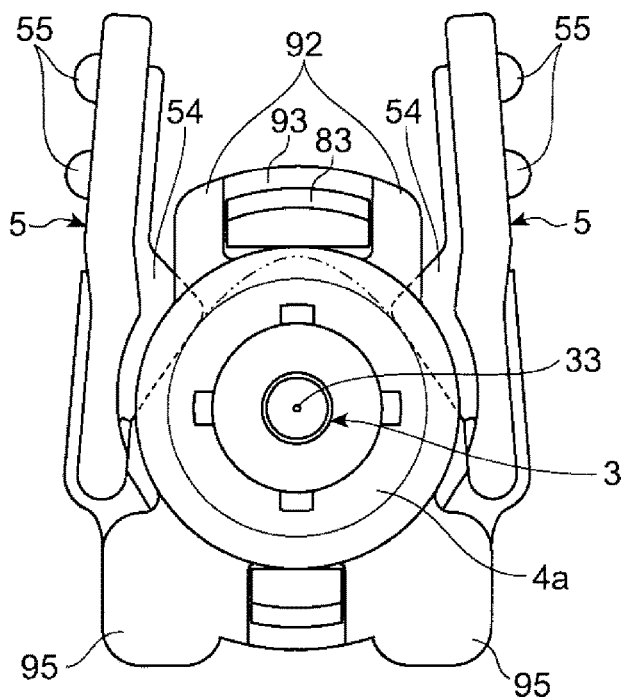
FIG. 22 is a view corresponding to FIG. 20, illustrating a state in which a pair of wings is displaced.
Figure 23:
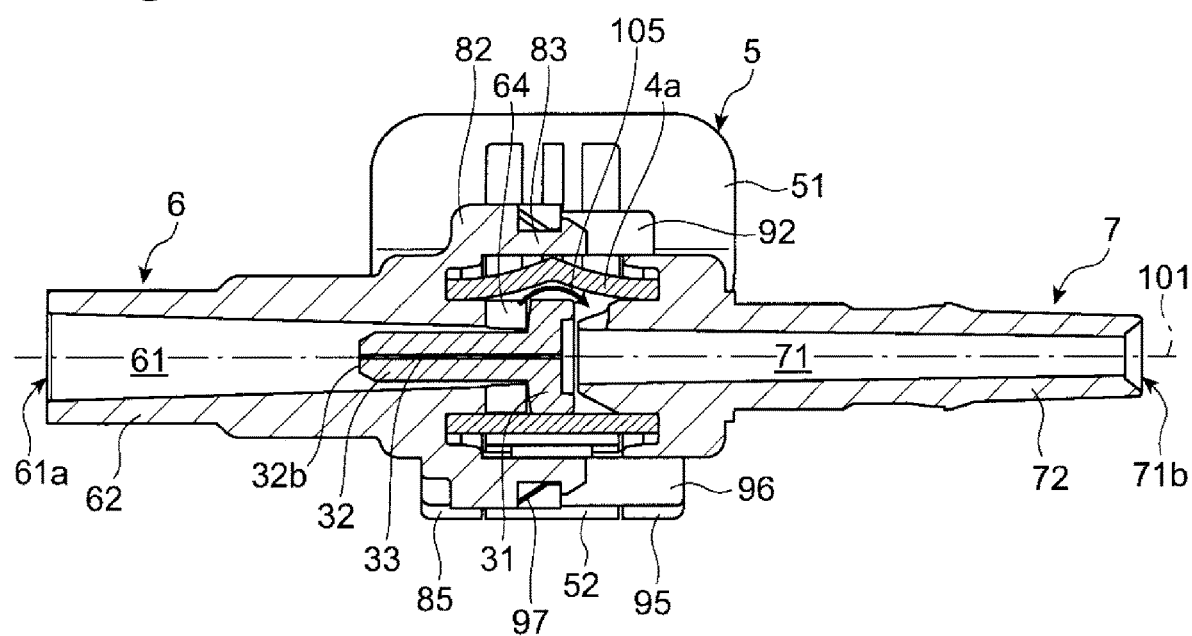
FIG. 23 is a view corresponding to FIG. 21, illustrating a state in which a pair of wings is displaced.

As illustrated in FIGS. 22 and 23, as for the operation of the elastic member 4a, when a user pinches and rotates the pair of wings 5, 5 inward toward the elastic member 4a, the side surface of the elastic member 4a is pressed, so that an upper portion of the elastic member 4a is deformed so as to form an upwardly convex curved surface, thereby forming a gap between the inner periphery of the elastic member 4a and the outer periphery of the base 31 of the flow control device 3. This can form a bypass flow path 105 for a chemical liquid, connected from the first flow path 61 to the second flow path 71 through the upper slot groove 64, and a larger amount of chemical liquid can pass through the bypass flow path 105. In this way the flush device 1 can discharge and quickly flush more chemical liquid.

Similar procedure to that in the first embodiment can be used for assembling the flush device.

Other Embodiments

It should not be understood that the present invention is limited to the above-described embodiments. In addition, other embodiments may be configured by freely combining the features described in the above-described embodiments. Further, various improvements, changes and deletions in design may be applied to the above-described embodiments.

For example, a structure corresponding to the first coupler 8 may be provided in the second housing 7 and a structure corresponding to the second coupler 9 may be provided in the first housing 6. This configuration can also obtain effects similar to those in the above-described embodiments.

EXPLANATORY NOTE

1 FLUSH DEVICE
2 CASING
3 FLOW CONTROL DEVICE
31 BASE
32 PROTRUSION
32a BASE END (OF PROTRUSION)
32b LEADING END (OF PROTRUSION)
33 THROUGH HOLE
35 FITTING PROJECTION
36 SPACER
4, 4a ELASTIC MEMBER
41 TUBULAR PORTION
42 BLOCK PORTION
43 BUMP
5 WING
52 SHAFT PORTION
54 PRESSING PORTION
6 FIRST HOUSING
61 FIRST FLOW PATH
62 BODY (OF FIRST HOUSING)
63 DOWNSTREAM END PORTION (OF FIRST HOUSING)
65 HOLE
7 SECOND HOUSING
71 SECOND FLOW PATH
72 BODY (OF SECOND HOUSING)
73 UPSTREAM END PORTION (OF SECOND HOUSING)
8 FIRST COUPLER
9 SECOND COUPLER
10 IRRIGATION LINE
12 PRESSURE TRANSDUCER
101 CENTRAL AXIS (OF FIRST HOUSING)
102 CENTRAL AXIS (OF SECOND HOUSING)
103 CENTRAL AXIS (OF FLOW CONTROL DEVICE)
104 INTERVAL BETWEEN PROTRUSION AND INNER PERIPHERY OF FIRST HOUSING
105 BYPASS FLOW PATH

The invention claimed is:

1. A flush device comprising:
   a first housing provided with a first flow path having a central axis;
   a second housing provided with a second flow path extending along the central axis, the second housing being coupled to the first housing;
   a flow control device including:
     a base located between the first flow path and the second flow path;
     a protrusion having a base end on a side of the base and a leading end located inside the first flow path, the protrusion extending from the base end toward the leading end; and
     a through hole extending along the central axis through both the base and the protrusion to connect the first flow path to the second flow path in fluid communication; and an elastic member provided around the base of the flow control device to seal off a space between the first flow path and the second flow path, wherein the elastic member is configured to be deformable to form a gap between the elastic member and an outer periphery of the base of the flow control device, thereby forming a bypass flow path for further fluid communication between the first flow path and the second flow path, wherein the protrusion of the flow control device is provided on its outer periphery with a plurality of fitting projections at intervals in the circumferential direction, wherein the first housing has an inner periphery defining the first flow path, the inner periphery being provided with a plurality of fitting receiving portions at intervals in the circumferential direction, each being fitted to each of the plurality of fitting projections; and wherein the protrusion is disposed with a predetermined interval away from the inner periphery defining the first flow path.

2. The flush device according to claim 1, wherein a plurality of spacers are provided on the outer periphery of the protrusion and on the side of the base end of the plurality of fitting projections in the flow control device.

3. The flush device according to claim 2, wherein the plurality of spacers each butt the inner periphery defining the first flow path.

4. The flush device according to claim 1, wherein the first housing is coupled to the second housing by means of a coupling mechanism, and the coupling mechanism includes a claw provided at an end of one of the first housing and the second housing, and a claw receiving portion provided at an end of the other of the first housing and the second housing, the claw receiving portion being fitted to the claw.

5. The flush device according to claim 4, wherein the coupling mechanism includes an arm extending from the claw receiving portion toward one of the first housing and the second housing, and an arm receiving portion provided at an end of one of the first housing and the second housing to receive the arm for restricting relative rotation of the first housing with respect to the second housing.

6. The flush device according to claim 1, further comprising a pair of wings, the pair of wings each including:

a shaft portion extending parallel to the central axis, the pair of wings each being supported by the first housing and the second housing so as to rotate around the shaft portion; and a pressing portion for pressing and deforming the elastic member.

7. The flush device according to claim 1, wherein the elastic member includes a positioning marker provided integrally with the elastic member.

8. An irrigation line comprising:

the flush device according to claim 1.

* * * * *